(12) United States Patent
Heinz (10) Patent No.: US 7,776,045 B2
(45) Date of Patent: Aug. 17, 2010

(54) INSTRUMENTATION AND METHODS FOR VERTEBRAL DISTRACTION

(75) Inventor: Eric Steven Heinz, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1617 days.

(21) Appl. No.: 10/922,707

(22) Filed: Aug. 20, 2004

(65) Prior Publication Data

US 2006/0052793 A1 Mar. 9, 2006

(51) Int. Cl.
*A61B 17/56* (2006.01)

(52) U.S. Cl. .......................................................... 606/90

(58) Field of Classification Search ................... 606/57, 606/61, 90, 105, 246, 279, 86 A, 99
See application file for complete search history.

(56) References Cited

U.S. PATENT DOCUMENTS

| | | |
|---|---|---|
| 3,486,505 A | 12/1969 | Morrison |
| 4,386,603 A | 6/1983 | Mayfield |
| 4,736,738 A | 4/1988 | Lipovsek et al. |
| 4,898,161 A | 2/1990 | Grundei |
| 4,955,885 A | 9/1990 | Meyers |
| 5,122,130 A | 6/1992 | Keller |
| 5,192,327 A | 3/1993 | Brantigan |
| 5,235,966 A | 8/1993 | Jamner |
| 5,431,658 A | 7/1995 | Moskovich |
| 5,505,732 A | 4/1996 | Michelson |
| 5,554,191 A | 9/1996 | Lahille et al. |
| 5,599,279 A | 2/1997 | Slotman et al. |
| 5,697,889 A | 12/1997 | Slotman et al. |
| 5,722,977 A | 3/1998 | Wilhelmy |
| 5,755,732 A | 5/1998 | Green et al. |
| 5,944,658 A | 8/1999 | Koros et al. |
| 6,004,326 A | 12/1999 | Castro et al. |
| 6,083,225 A | 7/2000 | Winslow et al. |
| 6,096,038 A | 8/2000 | Michelson |
| 6,174,311 B1 | 1/2001 | Branch et al. |
| 6,179,873 B1 | 1/2001 | Zientek |
| 6,224,599 B1 | 5/2001 | Baynham et al. |
| 6,224,607 B1 | 5/2001 | Michelson |
| 6,261,296 B1 | 7/2001 | Aebi et al. |
| 6,270,498 B1 | 8/2001 | Michelson |
| 6,332,887 B1 | 12/2001 | Knox |
| 6,395,034 B1 | 5/2002 | Suddaby |
| 6,436,101 B1 | 8/2002 | Hamada |
| 6,478,800 B1 | 11/2002 | Fraser et al. |
| 6,514,260 B1 | 2/2003 | Zdeblick et al. |
| 6,565,574 B2 | 5/2003 | Michelson |
| 6,595,995 B2 | 7/2003 | Zdeblick et al. |
| 6,610,065 B1 | 8/2003 | Branch et al. |

(Continued)

FOREIGN PATENT DOCUMENTS

EP 0 531 710 A2 3/1993

(Continued)

*Primary Examiner*—Eduardo C Robert
*Assistant Examiner*—David Comstock (57) ABSTRACT

An instrument for distracting vertebrae includes a shaft assembly and a distraction assembly at a distal end of the shaft assembly. The distraction assembly includes first and second distraction members movable from an unexpanded configuration for insertion toward an expanded configuration to separate the vertebrae. The shaft assembly is movable relative to the distraction assembly to facilitate placement of the distraction assembly in the disc space.

23 Claims, 6 Drawing Sheets

U.S. PATENT DOCUMENTS

| | | |
|---|---|---|
| 6,635,060 B2 | 10/2003 | Hanson et al. |
| 6,641,582 B1 | 11/2003 | Hanson et al. |
| 6,641,614 B1 | 11/2003 | Wagner et al. |
| 6,652,533 B2 | 11/2003 | O'Neil |
| 2001/0010001 A1 | 7/2001 | Michelson |
| 2001/0029377 A1* | 10/2001 | Aebi et al. ............... 606/105 |
| 2002/0082695 A1 | 6/2002 | Neumann |
| 2002/0116009 A1 | 8/2002 | Fraser et al. |
| 2002/0138078 A1 | 9/2002 | Chappuis |
| 2002/0177897 A1 | 11/2002 | Michelson |
| 2003/0028197 A1 | 2/2003 | Hanson et al. |
| 2003/0045884 A1 | 3/2003 | Robie et al. |
| 2003/0083664 A1 | 5/2003 | Rogers et al. |
| 2003/0130737 A1 | 7/2003 | McGahan et al. |
| 2003/0149438 A1 | 8/2003 | Nichols et al. |
| 2003/0187448 A1 | 10/2003 | Michelson |
| 2003/0195517 A1 | 10/2003 | Michelson |
| 2003/0195520 A1 | 10/2003 | Boyd et al. |
| 2003/0225416 A1 | 12/2003 | Bonvallet et al. |
| 2004/0002758 A1 | 1/2004 | Landry et al. |
| 2004/0030387 A1 | 2/2004 | Landry et al. |
| 2004/0087947 A1 | 5/2004 | Lim et al. |
| 2004/0092933 A1* | 5/2004 | Shaolian et al. ............... 606/61 |
| 2004/0117020 A1 | 6/2004 | Frey et al. |

FOREIGN PATENT DOCUMENTS

| | | |
|---|---|---|
| WO | WO 03/092507 | 11/2003 |

* cited by examiner

INSTRUMENTATION AND METHODS FOR VERTEBRAL DISTRACTION

BACKGROUND

Distraction of vertebrae can be employed to access the disc space or space between vertebrae for surgical procedures, to restore vertebral anatomy, to maintain spacing of the vertebrae during surgery, or to obtain the desired fit of implants and other devices to be implanted in the disc space or in the vertebral bodies. There remains a need for instruments and techniques that facilitate such distraction and the surgical procedures that employ distraction of vertebrae.

SUMMARY

According to one aspect, there is provided an instrument for distracting vertebrae that includes a shaft assembly and a distraction assembly at a distal end of the shaft assembly. The distraction assembly includes first and second distraction members movable from an unexpanded configuration for insertion in the disc space toward an expanded configuration to separate or distract the vertebrae.

According to another aspect, there is provided an instrument for distracting vertebrae that includes a shaft assembly and a distraction assembly. The shaft assembly is pivotal relative to the distraction assembly to assume any one of a plurality of orientations relative thereto.

According to another aspect, there is provided an instrument for distracting vertebrae that includes a shaft assembly and a distraction assembly. The shaft assembly includes a non-rigid shaft member coupled to the distraction assembly that is operable move the distraction assembly between an unexpanded configuration and an expanded configuration.

According to a further aspect, a method for distracting adjacent vertebrae of a spinal column includes: positioning a distraction assembly of a distraction instrument in a spinal disc space between the adjacent vertebrae along an approach defined by a plane bisecting the space between the adjacent vertebrae; expanding the distraction assembly with a shaft assembly of the distraction instrument to distract the adjacent vertebrae; and pivoting the shaft assembly of the distraction instrument relative to the distraction assembly transversely to the plane.

DESCRIPTION OF THE ILLUSTRATED EMBODIMENTS

For the purposes of promoting an understanding of the principles of the present invention, reference will now be made to the embodiments illustrated in the drawings and specific language will be used to describe the same. It will nevertheless be understood that no limitation on the scope of the invention is intended, and any alterations or modifications in the disclosed embodiments and further applications of the principles of the invention are contemplated as would normally occur to one skilled in the art to which the invention relates.

Referring to FIGS. 1-4, there is shown a distraction instrument 20 having a shaft assembly 22 extending along a longitudinal axis 21. Distraction instrument 20 includes a distraction assembly 40 at a distal end of shaft assembly 22. Distraction assembly 40 is positionable in a spinal disc space or other space between adjacent vertebrae of the spinal column in an unexpanded configuration. Distraction assembly 40 can be remotely manipulated with shaft assembly 22 by the surgeon to an expanded configuration to increase the separation distance and/or provide a desired angulation between the adjacent vertebral endplates. In one embodiment, shaft assembly 22 is moveable as indicated by arrows 106 to re-orient or re-position shaft assembly 22 along longitudinal axis 21 relative to distraction assembly 40 when distraction assembly 40 is in the disc space. Distraction instrument 20 is configured to maintain the ability to manipulate distraction assembly 40 with the re-oriented or re-positioned shaft assembly 22.

Distraction assembly 40 includes a first distraction member 42 and a second distraction member 44. In the illustrated embodiment, distraction members 42, 44 are plate-like members having opposite outer surfaces positionable toward and moveable against the endplate of an adjacent vertebrae. The distraction members 42, 44 provide a separation force to the adjacent vertebrae when moved away from one another toward the expanded configuration. Other forms for distraction members 42, 44 are also contemplated, including single blades, U-shaped blades, or other suitable structure for contacting the adjacent vertebral endplate.

Figures 1, 2:
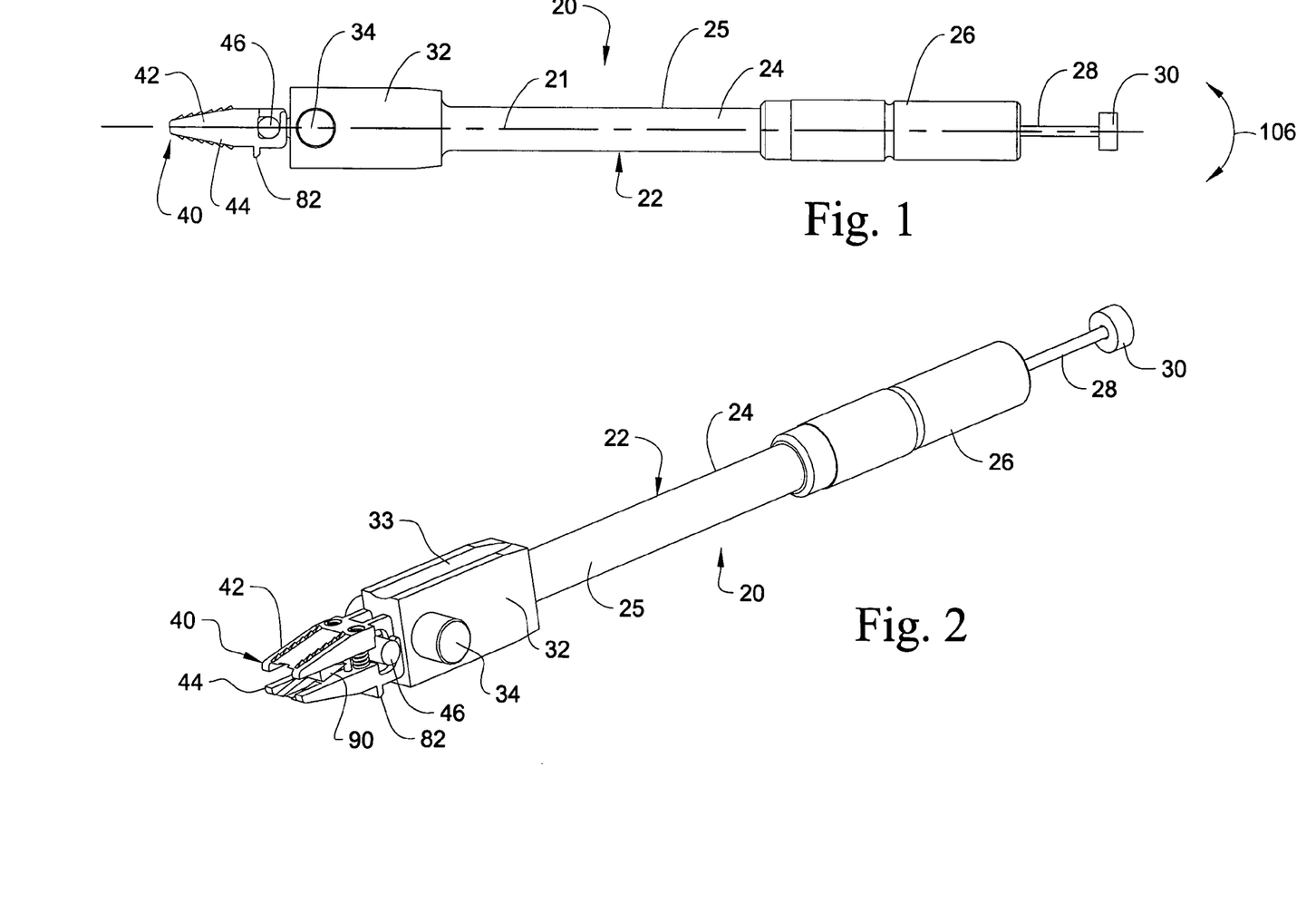
FIG. 1 is an elevation view of a distraction instrument in an unexpanded configuration.
FIG. 2 is a perspective of the distraction instrument of FIG. 1.
Figure 3:
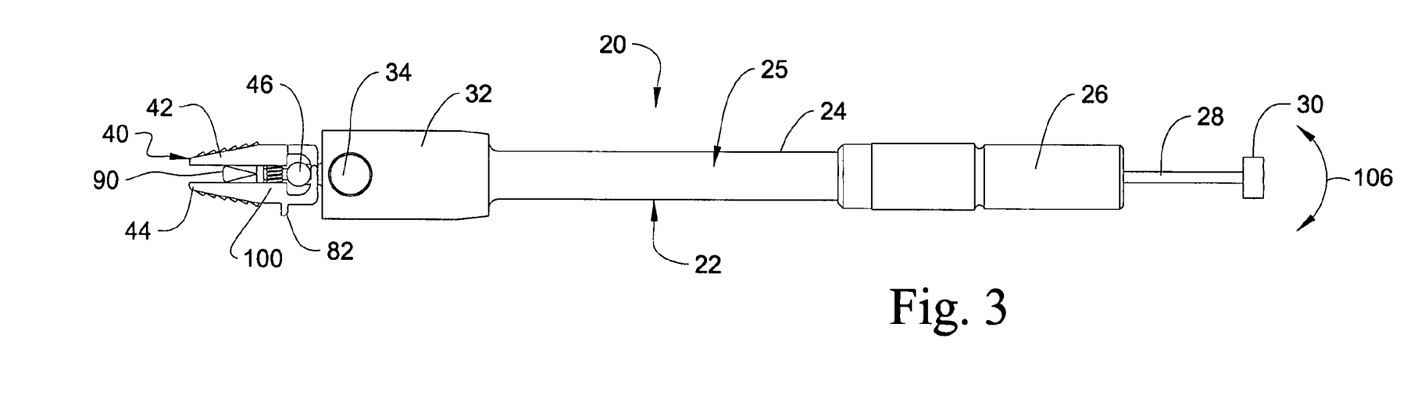
FIG. 3 is an elevation view of the distraction instrument of FIG. 1 in an expanded configuration.

Distraction members 42, 44 are movable relative to one another from an unexpanded configuration, as shown in FIG. 1, to an expanded configuration, as shown in FIGS. 2 and 3. In the unexpanded configuration, first and second distraction members 42, 44 are positioned adjacent one another to form a low profile configuration for insertion in the space between the vertebrae. In the expanded configuration, distraction members 42, 44 are moved away from one another into contact with the endplates of the vertebrae. In one embodiment, shaft assembly 22 includes a locking mechanism to maintain distraction members 42, 44 in the expanded configuration. The ability to re-orient or re-position shaft assembly 22 relative to distraction assembly 40 can facilitate access and viewing of the vertebrae and disc space during the surgical procedure. Distraction instrument 20 can further be employed in procedures where it may not be as desirable for shaft assembly 22 to extend from the disc space along an approach defined by a plane bifurcating the space between the adjacent vertebra.

With regard to shaft assembly 22, the illustrated embodiment includes a first shaft member 24 and a second shaft member 28. First shaft member 24 includes a proximal portion 26 and a distal portion 32. Proximal portion 26 can be cylindrical and enlarged relative to a cylindrical intermediate portion 25 of shaft member 24 extending distally therefrom to provide a platform to facilitate gripping of shaft member 24. In the illustrated embodiment, distal portion 32 is enlarged relative to intermediate portion 25 of shaft member 24. Distal portion 32 can further include an extension member 34 extending transversely to longitudinal axis 21 projecting laterally therefrom. Distal portion 32 includes a rectangular shape and extension member 34 includes a cylindrical shape in the illustrated embodiment. Other embodiments contemplate that one or more of distal portion 32 and proximal portion 26 are the same size and shape as intermediate portion 25, or are smaller in size and shape than intermediate portion 25.

Figure 4:
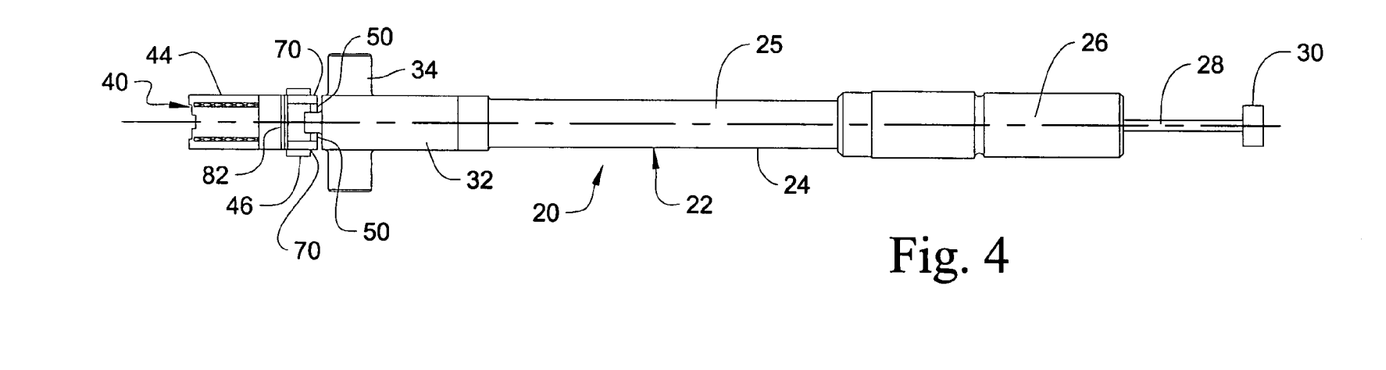
FIG. 4 is a plan view of the distraction instrument of FIG. 1.
Figure 15:
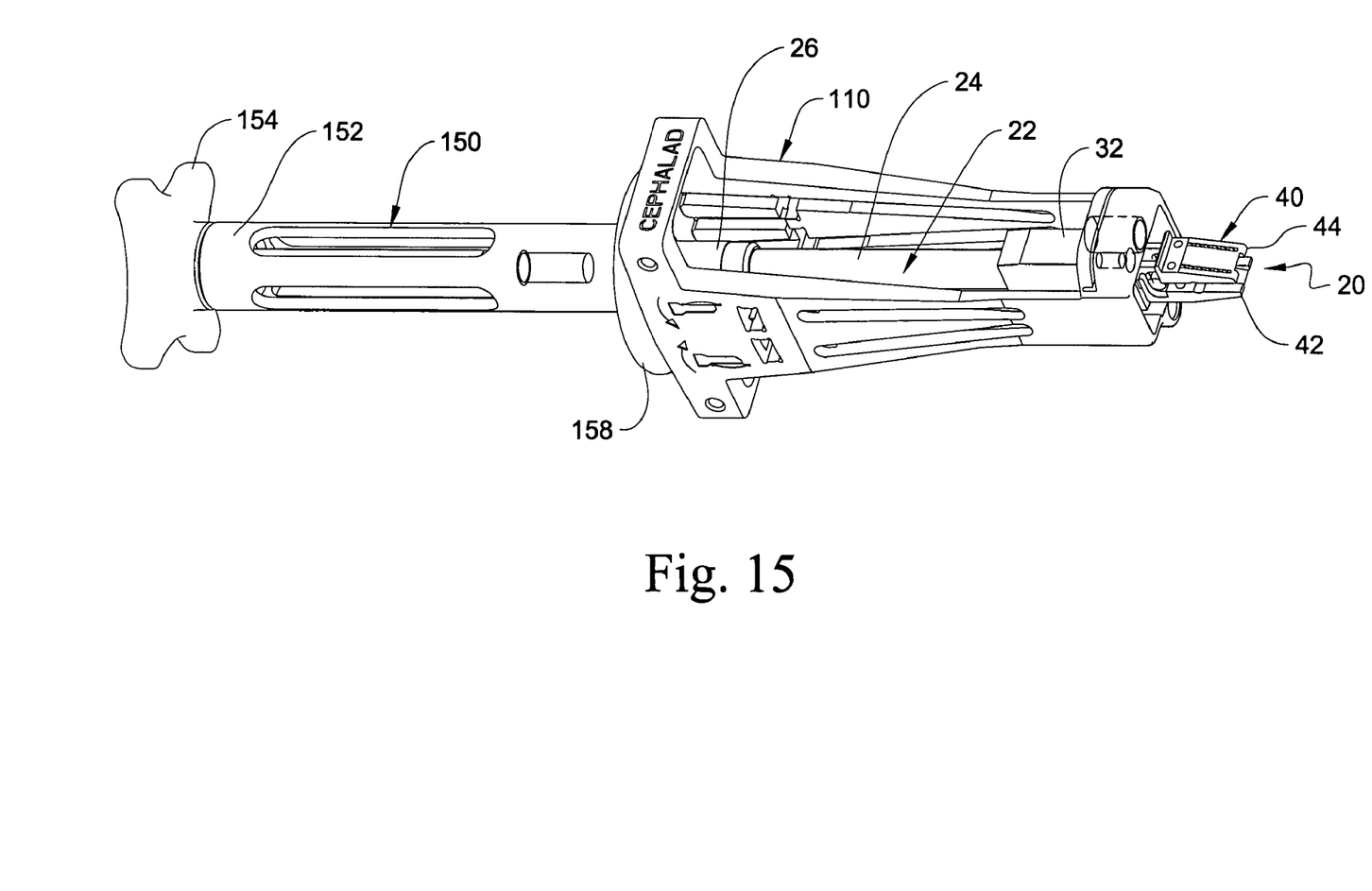
FIG. 15 is an elevation view of the distraction instrument and handle assembly of FIG. 14 with a milling guide positioned about the distraction instrument.

Distal portion 32 and extension member 34 can receive a milling guide 110 or other surgical instrument thereover, as shown in FIG. 15, such that the milling guide 110 is constrained from moving laterally or cephaladly/caudally relative to shaft assembly 22. As shown in FIG. 4, distal portion 32 includes a shallow groove 33 therein to facilitate placement and rotation of an instrument therealong, such as a drill, tap, burr, driver or other device. Other forms for distal portion 32 and extension member 34 are also contemplated to guide other instruments or devices.

A coupling arm 46 is provided at the distal end of distal portion 32, and engages distraction assembly 40 so that distraction assembly 40 is movable relative to shaft assembly 22, as discussed further herein. In the illustrated embodiment, coupling arm 46 is in the form a cylindrical bar extending transversely to longitudinal axis 21. Second shaft member 28 extends through first shaft member 24 and includes an end member 30 at a proximal end thereof. The opposite end of second shaft member 28 extends through coupling member 46 to an actuating member 90 positioned between distraction members 42, 44. At least a portion of second shaft member 28 is non-rigid so that the portion of second shaft member 28 extending between coupling member 46 and actuating member 90 is bendable to allow distraction assembly 40 and shaft assembly 22 to be pivoted relative to another. In one embodiment, it is contemplated that second shaft member 28 is flexible along all or a portion of its length. In one specific embodiment, second shaft member 28 is a cable. Other embodiments contemplate other forms for second shaft member 28, including one or more wires, strands, tethers, rods, hollow members, rods, chains, ropes, sutures, or cords, for example.

Second shaft member 28 is movable relative to first shaft member 24 to displace actuating member 90 between distraction members 42, 44. In one embodiment, a proximally directed force to end member 30 pulls actuating member 90 proximally between distraction members 42, 44 to move distraction assembly 40 from its unexpanded configuration to its expanded configuration. The proximally directed force can be applied manually to second shaft member 28, or via a mechanical device such as a cable tensioner, for example.

First and second distraction members 42, 44 are shown in further detail in FIGS. 5-11. Distraction member 44 includes a pair of proximal arms 70 extending from a body 45. Arms 70 are spaced from one another on opposite sides of longitudinal axis 21, and each includes an L shape having a first portion extending from body 45 and a second portion formed by the lower leg of the L that extends toward the other distraction member 42.

Figure 5:
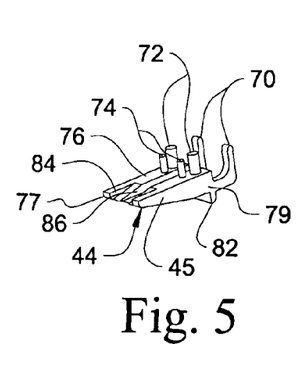
FIG. 5 is a perspective view of a distraction member comprising a portion of the distraction instrument of FIG. 1.
Figure 6:
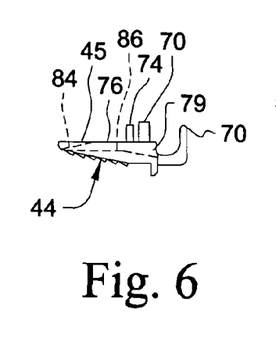
FIG. 6 is an elevation view of the distraction member of FIG. 5.
Figure 7:
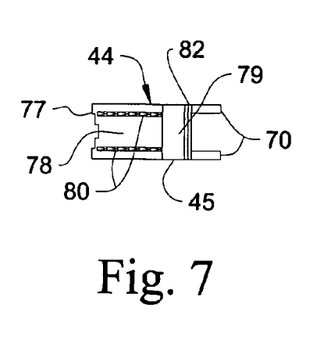
FIG. 7 is a plan view looking toward an outer surface of the distraction member of FIG. 5.

As shown in FIGS. 5-7, body 45 includes an inner surface 76 and an opposite outer surface 78. Outer surface 78 includes engaging members 80 therealong. In the illustrated embodiment, engaging members 80 comprise a pair of rows of projections projecting outwardly from outer surface 78 that extend from a distal end 77 of body 45 to a proximal body portion 79. Other forms for engaging members 80 are also contemplated, including teeth, ridges, valleys, spikes, raised surfaces, indentations, knurlings, surface roughenings, and combinations thereof that extend along all or a portion of outer surface 78. A distraction member 44 without engaging members 80 is also contemplated.

When distraction member 44 is in its FIG. 1 orientation relative to shaft assembly 22, inner surface 76 extends parallel to an extension of longitudinal axis 21. Outer surface 78 is sloped relative to longitudinal axis 21 such that body 45 includes a smaller thickness at its distal end 77 than at proximal body portion 79. Along proximal body portion 79, outer surface 78 extends generally parallel to longitudinal axis 21.

Body 45 includes a pair of proximal pins 72 that extends from inner surface 76 toward distraction member 42. Body 45 further includes a pair of distal pins 74 extending from inner surface 76 toward distraction member 42. Distal pins 74 are spaced distally from proximal pin 72. The pins of the corresponding pairs of pins 72, 74 are separated from one another by an intermediate wedge slot 86 formed in inner surface 76. Wedge slot 86 extends from distal end 77 of body 45 to the proximal end of body 45. A wedge receptacle 84 is formed in inner surface 76 adjacent distal end 77 of body 45. Wedge receptacle 84 is sloped relative to inner surface 76 and terminates at inner surface 76 at a location spaced distally of distal pins 74.

Figure 8:
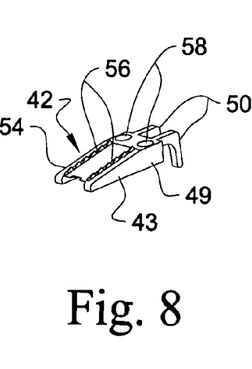
FIG. 8 is a perspective view of another distraction member comprising a portion of the distraction instrument of FIG. 1.
Figure 9:
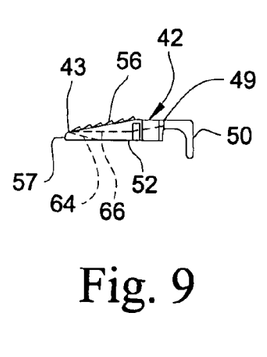
FIG. 9 is an elevation view of the distraction member of FIG. 8.
Figure 10:
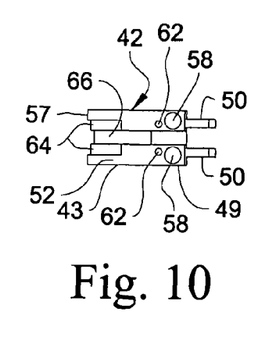
FIG. 10 is a plan view looking toward an outer surface of the distraction member of FIG. 8.

As shown in FIGS. 8-10, distraction member 42 includes a body 43 and a pair of proximal arms 50 extending proximally from body 43. Arms 50 are spaced from one another on opposite sides of longitudinal axis 21, and each includes an L shape having a first portion extending from body 43 and a second portion formed by the lower leg of the L that extends toward the other distraction member 44. When engaged to shaft assembly 22, arms 50 are positioned between arms 70 of distraction member 44, as shown in FIG. 4. Other arrangements are contemplated, such as arms 70 being positioned between arms 50, or one of arms 50 is located outside (relative to longitudinal axis 21) an adjacent one of the arms 70 and the other of the arms 50 is located inside (relative to longitudinal axis 21) of the other of the arms 70.

Coupling member 46 is received between bodies 43, 45 of distraction members 42, 44 and the second portion of arms 50, 70 formed by the proximal lower legs of the L-shaped arms. Arms 50, 70 and thus distraction members 42, 44 are rotatable about coupling member 46 to allow shaft assembly 22 to be moved relative to distraction assembly 40. Other coupling arrangements are contemplated, such as, for example, arms 50, 70 that form ears extending completely about coupling member 46.

Body 43 includes an inner surface 52 and an opposite outer surface 54. Outer surface 54 includes engaging members 56 therealong. In the illustrated embodiment, engaging members 56 comprise a pair of rows of projections extending outwardly from outer surface 54 that extend from a distal end 57 of body 43 to a proximal body portion 49. Other forms for engaging members 56 are also contemplated, including teeth, ridges, valleys, spikes, raised surfaces, indentations, knurlings, surface roughenings, and combinations thereof that extend along all or a portion of outer surface 54. A distraction member 42 without engaging members 56 is also contemplated.

When in its FIG. 1 orientation relative to shaft assembly 22, inner surface 52 extends parallel to longitudinal axis 21 and outer surface 54 is sloped relative to longitudinal axis 21 such that body 43 includes a smaller thickness at distal end 57 than at proximal body portion 49. Along proximal body portion 49 Outer surface 54 extends generally parallel to longitudinal axis 21.

When distraction members 42, 44 are assembled to shaft assembly 22, their outer surfaces 56, 78 are sloped relative to the respective inner surfaces 52, 76 such that bodies 43, 45 taper distally from their proximal body portions 49, 79. When in the unexpanded configuration of FIG. 1, the distal ends 57, 77 of distraction members 42, 44 form a reduced profile leading end nose to facilitate insertion of distraction assembly 40 into the space between vertebrae. Furthermore, the sloped outer surfaces 56, 78 mimic the angulation between the vertebral endplates that is desired when distraction members 42, 44 are moved toward their expanded configuration of FIGS. 2 and 3. Other embodiments contemplate configurations where outer surfaces 56, 78 are parallel to one another when distraction members 42, 44 are assembled with shaft assembly 22. Further embodiments contemplate configurations where outer surfaces 56, 78 are sloped along their entire length between the distal and proximal ends of distraction members 42, 44. Still other embodiments contemplate configurations wherein outer surfaces 56, 78 are sloped to form a distraction assembly 40 that tapers proximally. Other embodiments contemplate configurations where the inner and outer surfaces of each of the distraction members 42, 44 are parallel to one another, or are sloped to taper proximally.

Distraction member 42 includes a pair of proximal bores 58 extending from inner surface 52 into body 43. Proximal bores 58 are positioned to receive respective ones of the proximal pins 72 when distraction member 42 is assembled with distraction member 44. Body 43 further includes a pair of distal bores 62 extending from inner surface 52 into body 43. Distal bores 62 are positioned to receive respective ones of the distal pins 74 of distraction member 44 when distraction members 42, 44 are assembled. Springs 100 are receive in proximal bores 58, and are positioned about pins 72. Springs 100 are engaged between distraction members 42, 44 to bias distraction members 42, 44 toward the unexpanded configuration of FIG. 1. The interface between pins 72, 74 and bores 58, 62 resists distraction members 42, 44 from twisting or rotating relative to one another when assembled. The interface between pins 72, 74 and bores 58, 62 also maintains distraction members 42, 44 in proximal and distal relation to one another while allowing distraction members 42, 44 to be moved away from one another in parallel relation to the expanded configuration.

Each of the pairs of bores 58, 62 are spaced on opposite sides of a wedge slot 66 formed in inner surface 52 of distraction member 42. Wedge slot 66 extends from distal end 57 of body 43 to the proximal end of body 43. A wedge receptacle 64 is formed in inner surface 52 adjacent distal end 57 of body 43. Wedge receptacle 64 is sloped relative to inner surface 52 and terminates at inner surface 52 at a location spaced distally of distal pins 74. When distraction members 42, 44 are assembled wedge slots 66, 86 and wedge receptacles 64, 84 align with one another to receive actuating member 90.

Figure 11:
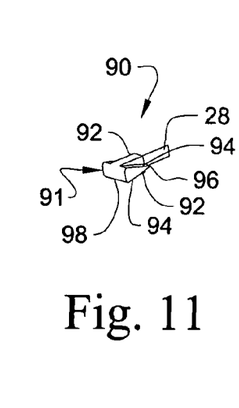
FIG. 11 is a perspective view of an actuating member comprising a portion of the distraction instrument of FIG. 1.

In FIG. 11 there is shown actuating member 90 in the form of a wedge 91 that includes a proximal end 96 engaged to a distal end of second shaft member 28. Wedge 91 includes opposite outer wedge surfaces 94 that taper proximally from a distal end 98 to proximal end 96. A rail 92 projects from each of the wedge surfaces 94 and is received in wedge slots 66, 86 of distraction members 42, 44 when positioned therebetween. Rail 92 interacts with wedge slots 66, 86 to maintain wedge 91 in alignment between distraction members 42, 44 as it is moved distally and proximally between distraction members 42, 44.

Wedge surfaces 94 are positioned in contact with inner surfaces 52, 76 of distraction members 42, 44. In the unexpanded configuration of FIG. 1, wedge 91 is received in wedge receptacles 64, 84, allowing distraction members 42, 44 to be positioned in the unexpanded configuration with inner surfaces 52, 76 adjacent to or in contact with one another. To move distraction members 42, 44 toward the expanded configuration of FIGS. 2 and 3, second shaft member 28 is displaced proximally relative to first shaft member 24, pulling wedge 91 proximally between distraction members 42, 44. Wedge surfaces 94 act on inner surfaces 52, 76 to move distraction members 42, 44 away from one another toward the expanded configuration. Proximal end 96 contacts distal pins 74 to limit further proximal movement of actuating member 90 when distraction members 42, 44 are in their expanded configuration.

To move distraction members 42, 44 from the expanded configuration to the unexpanded configuration, second shaft member 28 is released to allow wedge 91 to move distally between distraction members 42, 44. Wedge 91 is distally moveable via the force of springs 100 acting thereon. Distraction members 42, 44 can then move toward one another toward the unexpanded configuration as wedge 91 is displaced distally therebetween and into wedge receptacles 64, 84.

To prevent over-insertion of distraction assembly 40 into the space between vertebrae, one of the distraction members 42, 44 can be provided with a depth stop. In the illustrated embodiment, distraction member 44 includes a depth stop 82 projecting from outer surface 78 adjacent the proximal end of body 45. Depth stop 82 forms a lip that contacts the vertebral body to prevent over-insertion of distraction assembly 40 into the disc space. It is further contemplated that depth stop 82 could be provided on distraction member 42, that both distraction members 42, 44 include a depth stop, or that neither distraction member 42, 44 includes a depth stop.

As discussed above, coupling member 46 is received between arms 50, 70 of distraction members 42, 44. Arms 50, 70, and thus distraction members 42, 44, are pivotal about coupling member 46. Accordingly, shaft assembly 22 can be pivoted as indicated by arrows 106 in FIGS. 1 and 3 to adjust the relative orientation of shaft assembly 22 and distraction assembly 40.

Figure 12:
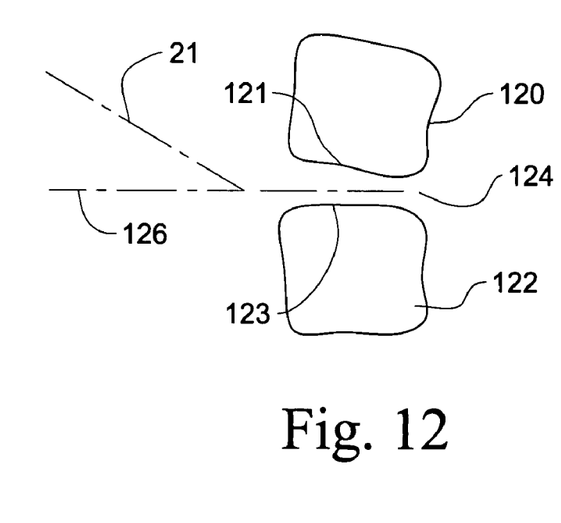
FIG. 12 is a diagram showing approaches to a spinal disc space between adjacent vertebrae with the distraction instrument of FIG. 1.

In one embodiment, shaft assembly 22 is moveable so that the longitudinal axis 21 of shaft assembly 22 is angled relative to a plane extending between and parallel to inner surfaces 52, 76 of distraction members 42, 44. This allows the surgeon to take an approach to the disc space that is not necessarily aligned with a plane bifurcating the space between the endplates of the adjacent vertebrae. For example, FIG. 12 shows a diagram with vertebrae 120, 122 and a disc space 124 therebetween. The endplates 121, 123 of vertebrae 120, 122 are angled relative to one another, although applications with parallel or oppositely inclined vertebral endplates are also contemplated. Endplates 121, 123 are bisected by a plane including axis 126 lying therein. When distraction assembly 40 is positioned in disc space 124, distraction members 42, 44 lie along axis 126 and are moved parallel or generally parallel thereto to distract vertebrae 120, 122. Shaft assembly 22 can be oriented so that longitudinal axis 21 of shaft assembly 22 lies along the plane including axis 126. Shaft assembly 22 can also be manipulated with distraction assembly 40 in either the expanded or unexpanded configuration so that longitudinal axis 21 is angled relative the plane including axis 126, as shown in FIG. 12.

Distraction instrument 20 can be employed in anterior approaches to the spinal column, although applications in other approaches are contemplated, including posterior, posterior-lateral, lateral and anterior-oblique approaches. Distraction instrument 20 has applications in the cervical, thoracic, lumbar, and lumbar-sacral regions of the spinal column. Distraction instrument 20 can be employed in conjunction with surgical procedures that include annulotomies, discectomies, cutting, scraping reaming, drilling, milling, chiseling, bone resection, and any other procedures to prepare the disc space and/or vertebral bodies to receive an implant. The implant can be an artificial disc device, an interbody fusion device, a plate, rod, or another device employed in spinal surgical procedures where disc space distraction is performed.

Figure 13:
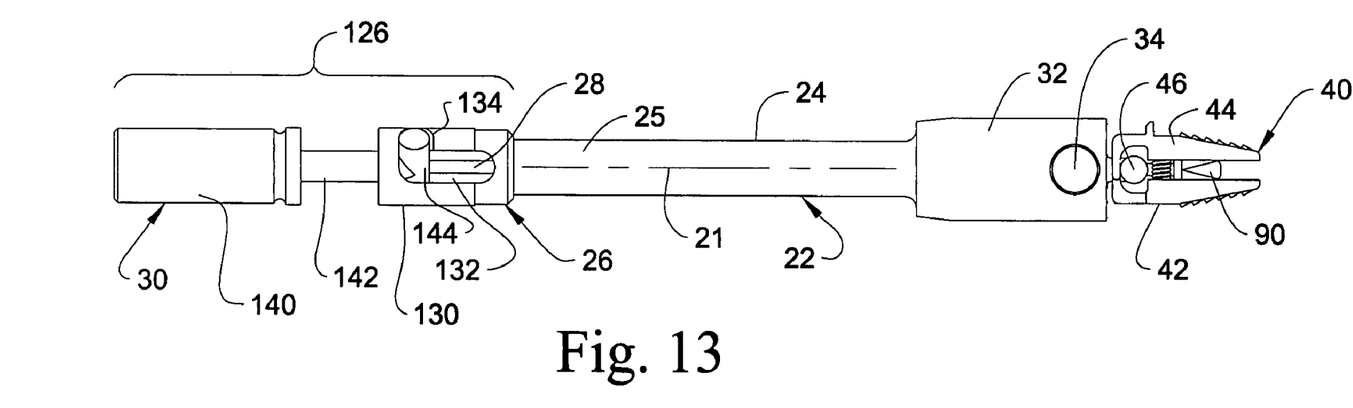
FIG. 13 is an elevation view of the distraction instrument of FIG. 1 with another embodiment proximal portion.

Referring now to FIG. 13, there is shown another embodiment of instrument 20 including an actuating assembly 126 operable to move actuating member 90 between distraction members 42, 44. In this embodiment, proximal portion 26 of first shaft member 24 and end member 30 of second shaft member 28 are modified from the embodiment shown in FIGS. 1-4. Proximal portion 26 includes a housing portion 130, and end member 30 includes a distal portion movably received in housing portion 130 and a proximal portion that projects proximally from housing portion 130. Housing portion 130 includes a translation slot 132 opening therealong and in communication with a central passage of housing portion 130. Translation slot 132 is elongated along the longitudinal axis 21, and includes a keyed portion 134 at a proximal end thereof that extends transversely to the elongated portion of translation slot 132.

The proximal portion of end member 30 includes a handle 140. A shaft 142 extends from handle 140 through a proximal end opening of housing portion 130. The distal portion of end member 30 includes a locking member 144 at a distal end of shaft 142. Second shaft member 28 is coupled to locking member 144. Locking member 144 extends transversely to and projects from shaft 142 to form a T-bar element that is slidingly received in translation slot 132 of housing portion 130. Locking member 144 interacts with translation slot 132 to prevent end member 30 from rotating in housing portion 130 until locking member 144 is positioned adjacent keyed portion 134 of translation slot 132.

Locking member 144 is movable proximally along translation slot 132 to apply a tension or pulling force to second shaft member 28, thus translating it and actuating member 90 proximally to move distraction members 42, 44 toward the expanded configuration. When locking member 144 contacts the proximal end of translation slot 132, further separation of distraction members 42, 44 is prevented. Handle 140 of end member 30 can then be rotated to position locking member 144 in keyed portion 134 of translation slot 132. In this position, locking member 144 is maintained in position relative to housing portion 130 by keyed portion 134. This locks the positioning of second shaft member 28 relative to first shaft member 24, and also the positioning of actuating member 90 between the expanded distraction members 42, 44. Handle 140 can be released and other procedures performed while distraction instrument 20 maintains distraction.

When it is desired to remove distraction assembly 40 from the disc space, handle member 140 is rotated to displace locking member 144 from keyed portion 134 and into the elongated portion of translation slot 132. Actuating member 90 can then be displaced distally along distraction members 42, 44 to allow distraction members 42, 44 to return toward their unexpanded figuration. Second shaft member 28 may not be sufficiently rigid to transmit a distally directed force applied to the proximal end of second shaft member 28 to distally displace actuating member 90. Accordingly, a force can be applied to distraction members 42, 44 to act on actuating member 90 and distally displace it to move distraction members 42, 44 toward their unexpanded configuration. For example, springs 100 can provide the necessary force to displace actuating member 90 distally between distraction members 42, 44 when tension on second shaft member 28 is released. When distraction members 42, 44 are positioned adjacent one another, further displacement of actuating member 90 is stopped, and actuating member 90 is housed in wedge receptacles 64, 84. Removal of distraction assembly 40 is facilitated as distraction members 42, 44 are moved toward the unexpanded configuration.

Figure 14:
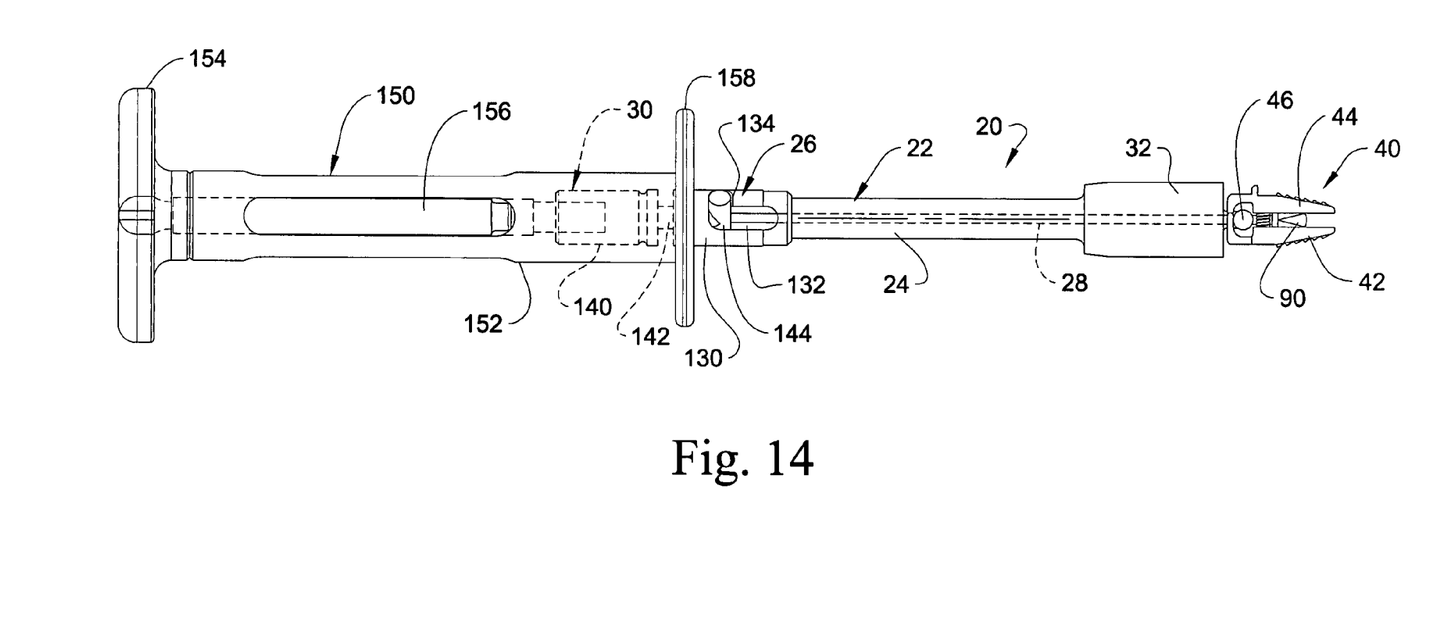
FIG. 14 is an elevation view of the distraction instrument of FIG. 13 with a handle assembly engaged thereto.

In FIG. 14 there is shown the distraction instrument 20 of FIG. 13 with a handle assembly 150 mounted thereto to provide a mechanical advantage in delivering the necessary tension or pulling force to second shaft member 28 move distraction assembly 40 to the expanded configuration. In particular, sufficient force to actuating member 90 is supplied to displace wedge 91 proximally between distraction members 42, 44 against the resistance supplied when distraction members 42, 44 contact the endplates of the adjacent vertebrae.

Handle assembly 150 includes an outer member 152 and a distal flange member 158 positioned about housing portion 130 of first shaft member 24. Handle assembly 150 further includes a proximal handgrip 154 rotatably coupled to a proximal end of outer member 152. An engaging member 156 extends from handle 154 through outer member 152, and is rotatable therein with handgrip 154. Engaging member 156 includes a distal end engageable to a proximal end of handle 140 of end member 30 by, for example, a threaded connection. As engaging member 156 is threadingly advanced in or over handle 140, end member 30 is displaced proximally in housing portion 130 and along engaging member 156, which tensions second shaft member 28 and displaces it and actuating member 90 proximally. When locking member 144 contacts the proximal end of translation slot 132, further rotation of handgrip 154 is resisted. Handgrip 154 can then be turned in the opposite direction to position locking member 144 in keyed portion 134 of translation slot 132 as discussed above.

In one example of a surgical procedure, distraction instrument 20 is positioned in a spinal disc space between adjacent vertebrae with distraction assembly 40 in the unexpanded configuration. The distal ends of first and second distraction members 42, 44 of distraction instrument 20 can be aligned, or nearly aligned, with the distal edge of the vertebral bodies opposite the approach of the instrument into the disc space. Depth stop 82 contacts the proximal edge of at least one of the adjacent vertebrae to limit or prevent over-insertion of distraction assembly 40 into the disc space. Proper positioning of instrument 20 may be confirmed with a lateral X-ray or other viewing system or technique.

Shaft assembly 22 is operable to displace actuating member 90 proximally between distraction members 42, 44 to move distraction assembly 40 to the expanded configuration. Distraction members 42, 44 act on respective ones of the adjacent vertebral endplates to separate or distract the adjacent vertebrae. The vertebrae and/or the disc space can then be prepared for engagement with or receipt of a spinal implant while distraction assembly 40 maintains the vertebral distraction. For example, FIG. 15 shows milling guide 110 positioned about distraction instrument 20. Milling guide 110 may be employed while distraction instrument 20 maintains distraction of the vertebrae. A guide sleeve may be employed to provide a protected pathway to the disc space if desired, although any surgical approach is contemplated, including minimally invasive and invasive approaches.

When desired to remove distraction assembly 40 from the disc space, actuating member 90 is released so that distraction members 42, 44 move toward their unexpanded configuration, displacing actuating member 90 distally therebetween. One or more shims or other temporary distractor(s) may be positioned between the adjacent vertebral bodies prior to removal of distraction instrument 20 to maintain distraction while a spinal implant is inserted in the disc space or engaged to the adjacent vertebrae. It is to be understood a wide variety of uses for distraction instrument 20 are contemplated. Distraction instrument 20 may be employed for disc space distraction and vertebral body preparation for insertion of one or more fusion cages, artificial discs, plates, bone spacers, or other devices positionable in the spinal disc space.

While the invention has been illustrated and described in detail in the drawings and foregoing description, the same is to be considered illustrative and not restrictive in character. All changes, equivalents, and modifications that come within the scope of the invention described herein are desired to be protected.

What is claimed is:

1. An instrument for distracting adjacent vertebrae, comprising:
a first distraction member positionable along an endplate of one of the adjacent vertebrae;
a second distraction member positionable along an endplate of the other of the adjacent vertebrae; and
a shaft assembly extending proximally from said first and second distraction members along a longitudinal axis, said shaft assembly including a coupling member at a distal end thereof with said first and second distraction members coupled to said coupling member, said shaft assembly being operable to move said distraction members relative to one another between an unexpanded configuration and an expanded configuration to separate the adjacent vertebrae, wherein said shaft assembly is pivotal about said coupling member to assume any one of a plurality of orientations relative to said first and second distraction members while said first and second distraction members are maintained in position relative to one another, wherein said first and second distraction members include at least two pins extending toward one another and at least two bores for receiving respective ones of said pins therein and further comprising at least one spring engaged between said first and second distraction members to bias said first and second distraction members toward said unexpanded configuration.

2. The instrument of claim 1, wherein said shaft assembly includes a first shaft member and a second shaft member extending through said first shaft member and said coupling member is mounted to a distal end of said first shaft member and said second shaft member extends through said coupling member to an actuating member positioned between said first and second distraction members.

3. The instrument of claim 2, wherein said actuating member is a proximally tapered wedge, said wedge having a distal position between said first and second distraction members in said unexpanded configuration and being movable proximally between said first and second distraction members to move said first and second distraction members to said expanded configuration.

4. The instrument of claim 2, wherein said second shaft member is flexible at least between said coupling member and said actuating member.

5. The instrument of claim 2, wherein said second shaft member includes a proximal end member engageable to displace said second shaft member and said actuating member proximally relative to said first shaft member and said first and second distraction members and said first shaft member includes a housing portion at a proximal portion thereof, said housing portion including a translation slot elongated proximally and distally therealong and said end member includes a locking member extending into said translation slot.

6. The instrument of claim 5, wherein said locking member is movable proximally along said translation slot from a first position wherein said first and second distraction members are in said unexpanded configuration to a second position wherein said first and second distraction members are in said expanded configuration.

7. The instrument of claim 6, wherein said translation slot includes a keyed portion extending transversely to said elongated portion thereof, said end member being rotatable relative to said housing portion to position said locking member in said keyed portion to maintain said first and second distraction members in said expanded configuration.

8. The instrument of claim 1, wherein said first and second distraction members each include a body and a pair of arms extending proximally from a proximal end of said body, each of said arms defining a receptacle for receiving said coupling member therein and each of said arms of said arm pairs includes a first portion extending proximally from said respective body and a second portion extending transversely to said first portion toward the other of said first and second distraction members, said first and second portions of each of said arms extending about said coupling member.

9. The instrument of claim 1, wherein said at least two pins and said at least two bores comprise four pins and four bores for receiving respective ones of said four pins, said pins and bores interacting with one another to maintain said first and second distraction members in alignment with one another during movement between said unexpanded and said expanded configurations.

10. An instrument for distracting adjacent vertebrae, comprising:
a first distraction member positionable along an endplate of one of the adjacent vertebrae;
a second distraction member positionable along an endplate of the other of the adjacent vertebrae; and
a shaft assembly extending proximally from said first and second distraction members along a longitudinal axis, said shaft assembly including a coupling member at a distal end thereof with said first and second distraction members coupled to said coupling member, said shaft assembly being operable to move said distraction members relative to one another between an unexpanded configuration and an expanded configuration to separate the adjacent vertebrae, wherein said shaft assembly is pivotal about said coupling member relative to said first and second distraction members to assume any one of a plurality of orientations relative to said first and second distraction members while said first and second distraction members are maintained in one of the unexpanded and expanded configurations, wherein said first and second distraction members include inner surfaces oriented toward one another, said inner surfaces defining a distal receptacle for receiving an actuating member when said first and second distraction members are in said unexpanded configuration and said first and second distraction members are spring-biased toward said unexpanded configuration, wherein said actuating member includes proximally tapered outer wedge surfaces in contact with adjacent ones of said inner surfaces of said first and second distraction members, said actuating member being movable proximally along said inner surfaces with said shaft assembly to move said distraction members from said unexpanded configuration to said expanded configuration and said inner surfaces of said first and second distraction members each define a slot extending therealong in communication with a respective one of said distal receptacles, said actuating member further including a rail extending from each of said wedge surfaces, said rails being received in respective ones of said slots to maintain said actuating member in alignment with said first and second distraction members.

11. An instrument for distracting adjacent vertebrae, comprising:
a first distraction member positionable along an endplate of one of the adjacent vertebrae;
a second distraction member positionable along an endplate of the other of the adjacent vertebrae;
an actuating member between said first and second distraction members; and
a shaft assembly including a first shaft member coupled to said first and second distraction members and a second shaft member coupled to said actuating member, said shaft assembly extending along a longitudinal axis proximally from said first and second distraction members along a longitudinal axis, said second shaft member and said actuating member being movable proximally relative to said first shaft member and said first and second distraction members to move said first and second distraction members from an unexpanded configuration to an expanded configuration, wherein at least a portion of said second shaft member is inoperable to displace said actuating member distally between said first and second distraction members in response to a distally directed force applied to said second shaft member proximally of said actuating member, wherein said first and second distraction members each include a body and a pair of arms extending proximally from a proximal end of said body, each of said arms defining, a receptacle for rotatably receiving said coupling member therein.

12. The instrument of claim 11, wherein said first shaft member is pivotally coupled to said first and second distraction members and said shaft assembly is movable relative to first and second distraction members to assume any one of a plurality of orientations relative to said first and second distraction members while said first and second distraction members are maintained in one of the unexpanded and expanded configurations and said shaft assembly further includes a coupling member at a distal end thereof and said first and second distraction members are pivotally coupled to said coupling member.

13. The instrument of claim 12, wherein said second shaft member extends distally of said coupling member between said coupling member and said actuating member, said second shaft member being flexible at least between said coupling member and said actuating member.

14. The instrument of claim 11, wherein said second shaft member is a flexible cable.

15. The instrument of claim 11, wherein said actuating member is a proximally tapered wedge, said wedge having a distal position between said first and second distraction members in said unexpanded configuration and being movable proximally: between said first and second distraction members to move said first and second distraction members toward said expanded configuration from said unexpanded configuration.

16. The instrument of claim 11, wherein said second shaft member includes a proximal end member engageable to displace said second shaft member and said actuating member proximally relative to said first shaft member and said first and second distraction members.

17. The instrument of claim 16, wherein said first shaft member includes a housing portion at a proximal portion thereof, said housing portion including a translation slot elongated proximally and distally therealong and said end member includes a locking member extending into said translation slot.

18. The instrument of claim 17, wherein said locking member is movable proximally along said translation slot from a first position wherein said first and second distraction members are in said unexpanded configuration to a second position wherein said first and second distraction members are in said expanded configuration.

19. The instrument of claim 18, wherein said translation slot includes a keyed portion extending transversely to said elongated portion thereof, said end member being rotatable relative to said housing portion to position said locking member in said keyed portion to maintain said first and second distraction members in said expanded configuration.

20. The instrument of claim 11, wherein said first and second distraction members include at least two pins and at least two bores for receiving respective ones of said pins therein and further comprising at least one spring engaged between said first and second distraction members to bias said first and second distraction members toward said unexpanded configuration.

21. The instrument of claim 20, wherein said at least two pins and said at least two bores comprise four pins and four bores for receiving respective ones of said four pins, said pins and bores interacting with one another to maintain said first and second distraction members in alignment with one another during movement between said unexpanded and said expanded configurations.

22. The instrument of claim 11, further comprising a spring engaged between said first and second distraction members to bias said first and second distraction members toward said unexpanded configuration.

23. The instrument of claim 11, wherein:
said first and second distraction members include inner surfaces oriented toward one another, said inner surfaces defining a distal receptacle for receiving said actuating member when said first and second distraction members are in said unexpanded configuration; and
said actuating member includes proximally tapered outer wedge surfaces in contact with said inner surfaces of said first and second distraction members, said actuating member being movable proximally along said inner surfaces with said shaft assembly to move said first and second distraction members from said unexpanded configuration to said expanded configuration.

* * * * *